United States Patent [19]

Reddy et al.

[11] Patent Number: 5,676,945
[45] Date of Patent: Oct. 14, 1997

[54] HUMAN LEUCINE-ZIPPER PROTEIN KINASE AND METHODS OF USE

[75] Inventors: Usharani Reddy, North Wales; David Pleasure, Wynnewood, both of Pa.

[73] Assignee: Children's Hospital of Philadelphia, Philadelphia, Pa.

[21] Appl. No.: 395,580

[22] Filed: Feb. 28, 1995

Related U.S. Application Data

[63] Continuation-in-part of Ser. No. 205,018, Mar. 1, 1994.

[51] Int. Cl.$^6$ .............................. C12N 9/12; A61K 38/45
[52] U.S. Cl. .............................. 424/94.5; 435/194
[58] Field of Search .............................. 435/194; 424/94.5

[56] References Cited

PUBLICATIONS

Asano, T. et al., "Domains Responsible for the Differential Targeting of Glucose Transporter Isoforms", *J. Biol. Chem.* 1992, 267, 19636–19641.
Forman, B. et al, "A Domain Containing Leucine-Zipper--Like Motifs Mediate Novel In Vivo Interactions Between the Thyroid Hormone and Retinoic Acid Receptors", *Molecular Endocrinology* 1989, 3, 1610–1626.
Gabathuler and Kvist, "The Endoplasmic Reticulum Retention Signal of the E3/19K Protein of Adenovirus Type 2 Consists of Three Separate Amino Acid Segments at the Carboxy Terminus", *J. Cell Biol.* 1990, 111, 1803–1810.
Hunter, T. et al., "Protein Kinase C Phosphorylation of the EGF Receptor at a Throninc Residue Close to the Cytoplasmic Face of the Plasma Membrane", *Nature* 1984, 311, 480–483.
Jackson et al., "Identification of a Consensus Motif for Retention of Transmembrane Proteins in the Endoplasmic Reticulum", *The EMBO J.* 1990, 9, 3153–3162.
Kozak, M., "Possible Role of Flanking Nucleotides in Recognition of the AUG Initiator Codon by Eukaryotic Ribosomes", *Nucleic Acid Res.* 1981, 9, 5233–5252.
Krebs, E. and Beavo, "Phosphorylation–Dephosphorylation of Enzymes", *Annu. Rev. Biochem.* 1979, 48, 923–959.

Lindberg, R. and Hunter, "cDNA Cloning and Characterization of eck, an Epithelial Cell Receptor Protein–Tyrosine Kinase in the eph/elk Family of Protein Kinases", *Mol. and Cell. Biol.* 1990, 10(11), 6316–6324.
Lindberg, R. et al., "Dual–Specificity Protein Kinases: Will Any Hydroxyl Do?" *Trends Biochem. Sci.* 1992, 17, 114–119.
Morrison, D. et al., "Direct Activation of the Serine/Threonine Kinase Activity of Raf–1 through Tyrosine Phosphorylation by the PDGF β–Receptor", *Cell* 1989, 58, 649–657.
Pelham, H.R.B., "Control of Protein Exit from the Endoplasmic Reticulum", *Annu. Rev. Cell Biol.* 1989, 5, 1–23.
Pleasure, S. et al., "Pure Posmitiotic, Polarized Human Neurons Derived from NTera 2 Cells Provide a System for Expressing Exogenous Proteins in Terminally Differentiated Neurons", *J. Neuroscience* 1992, 12, 1802–1814.
Rossomando, A. et al., "Evidence that pp42, a Major Tyrosine kinase Target Protein, is a Mitogen–Activated Serine/Threonine Protein Kinase", *PNAS USA* 1989, 86, 6940–6943.
Taylor et al, "Structural Framework for the Protein Kinase Family", *Annu. Rev. Cell Biol.* 1992, 8, 429–462.
Wernet, W. et al., "The cDNA of the Two Isoforms of Bovine cGMP–Dependent Protein Kinase", *FEBS* 1989, 251, 191–196.
Wickens, M. and Stephenson, "Role of the Conserved AAUAAA Sequence: Four AAUAAA Point Mutants Prevent Messenger RNA 3' End Formation", *Science* 1984, 226, 1045–1051.
Yarden, Y., "Growth Factor Receptor Tyrosine Kinases", *Ann. Rev. Biochem.* 1988, 57, 443–78.
Younkin, D. et al., "Inducible Expression of Neuronal Glutamate Receptor Channels in the NT2 Human Cell Line", *PNAS USA* 1993, 90, 2174–2178.

*Primary Examiner*—Keith D. Hendricks
*Attorney, Agent, or Firm*—Woodcock Washburn Kurtz Mackiewicz & Norris

[57] ABSTRACT

A novel protein kinase, leucine-zipper protein kinase, 668 amino acids in length is provided by the present invention. This protein kinase is localized to the human brain. Nucleic acid sequences encoding the protein kinase are also provided.

10 Claims, 5 Drawing Sheets

FIG. 1A

```
1    agcatcccgagcgagtgcagcagagcgcgctttgtgtgcgggcgagcccgagggcccagtgttc 74   accatcataccagggcagagagcagggcATGGCCTTGCATGAGACCCGAACACCCTTCTTTGGGGC
                                  M  A  C  L  H  E  T  R  T  P  S  F  G  G    16

147  TTTGTGTCTACCTAGTGAGGCCATGCGGAAGCTGGACCCAGATGACACTTCTGACTGCCCAGAAG
     F  V  S  T  L  S  E  A  S  M  R  K  L  D  P  D  T  S  D  C  T  P  E  K    40

220  ACCTGACCCCTACCCATGTCCTGCAGTTGCATGAGCAAGATGCAGGAGGACCAGGTGGAGCTTCAG
     D  L  T  P  T  H  V  L  Q  L  H  E  Q  D  A  G  G  P  G  G  A  G  S  P    65

293  TGAGGTGCGGAGCATCGAGTTGCAGTGCCAGTCAGGAGGCTTTCTTGAG
     E  S  R  A  S  R  V  R  A  D  E  V  R  L  Q  C  Q  S  G  G  F  L  E      89

366  GGCCTCTTCGGCTGCCTTCGGCCGGTCTGGACCATGATTGGCAAAGCTTACTCCACAGAGCAGC
     G  L  F  G  C  L  R  P  V  W  T  M  I  G  K  A  Y  S  T  E  H  K  Q  Q    113

439  AGGAAGACTTGGAGGTCCCTTTTGAGGAAATCCTTGATGATCTGCAGTGGGTCAGTGGGGCTCAGGGTGC
     Q  E  D  L  W  E  V  P  F  E  E  I  L  D  D  L  Q  W  V  G  S  G  A  Q  G  A   138

512  TGTCTTCCGGCTTCCAGGGAGAGGTGGAAGTCAAAGAAGAACGAAAGAACGATC
     V  F  L  G  R  F  H  G  E  E  V  A  V  K  K  V  R  D  L  K  E  T  D  I     162

585  AAGCCATTGGAAGCTGAAAGCTGACCAACATCATCACTTTCAAGGGAGTATGTCACCAGGCTCCTGCTACT
     K  H  L  R  K  L  K  H  P  N  I  I  T  F  K  G  V  C  T  Q  A  P  C  Y     186

658  GCATCCTCATGGAGTTCTGCGCGCAGGGGACAGGAGTACGAGGTGCTGCGGGCTGGCCGTCCTGTCACCCCT
     C  I  L  M  E  F  C  A  Q  G  Q  L  Y  E  V  L  R  A  G  R  P  V  T  P  S   211

731  CTTACTGGTTGACTGGTCCATGGCATGGTGGCATGAACTACTTGACCTGACAAGATTATCACAGG
```

```
     L L V D W S M G I A G G M N Y L H H K L I H R                                235
804  GATCTCAGTGCAGGATGGAGTATGGGAATAGCTGGAGGAATGAATTACCTTCATCACAAGCTCATTCACTTCCAAGG
     D L K S P N M L I T Y D D V V K I S D F G T S K                              259
877  ACTCAGTGATAAGAGCACAAAGATGCTTATCACATATGATGATGTTGTGAAGATTTCAGATTTTGGAACCTCAAAA
     E L S D K S T K M S F A G T V A W M A P E V I R N                            284
950  TGAACTGAGTGATAAGAGCACAAAGATGTCTTTTGCAGGAACAGTAGCCTGGATGGCCCCTGAAGTTATCCGGAAC
     E P V S E K V D I W S F G V V L W E L L T G E I                              308
1023 CCCTACAAGAGTGAATCTGAAGTCGATATATGGAGCTTTGGGGTGGTCCTGTGGGAGCTACTCATTGGTGAAATC
     P Y K D V D S S A I W G V G S N S L H L P V P                                332
1096 CCAGTGTCCGGATGGGTTTAAGATTCTCAGCTCTTGCAGCGCAATGCAACAACCACATGCTCCCGGTCCCTCCCATT
     S S C P D G F K I L L R Q C W N S K P R N R P S F                            357
1169 CCGACAGATGTCTGAGATTCTCAGCTCTTGCAGCTCTCATGTCTCACAGACCTTACTTTGAAG
     R Q I L L H L D I A S A D V L S T P Q E T Y F K                              381
1242 TCCCAGCAGATGCTCTGCATCTCGATATAGCTAGTGCAGATGTACTGTCTACTCCCCAGGAAACCTACTTCAAA
     S Q A E W R E E V K L H F E K I K S E G T C L H                              405
1315 GCCTAGAAGAGGAACTGGTGAAGCTTCATTGAGAAGATAAAGAGTGAAGGAACCTGTCTCCACTGATGA
```

```
       R  L  E  E  E  L  V  M  R  R  E  E  L  R  H  A  L  D  I  R  E  H  Y  E
1388 AGGAAGCTGGAGGAGGAGCTGGTCATGAGGAGGGAGGAGCTGCGACATGCCCTGGACATCAGAGAGCATTATGAGGAG 430

R  K  L  E  R  A  N  N  L  Y  M  E  Ⓛ  N  A  L  M  L  Q  Ⓛ  E  L  K  E
1461 AGGAAGCTGGAACGAGCCAACAACCTCTACATGGAGCTGAATGCCCTGATGCTGCAGCTGGAACTCAAGGAG 454

R  E  Ⓛ  R  R  E  Q  A  Ⓛ  E  R  R  C  P  G  L  L  K  P  H  P  S  R
1534 CGCGAGCTGCGCCGCGAGCAGGCCCTGGAGCGCCGCTGCCCAGGACTGCTGAAGCCACACCCCAGCCGG 478

G  L  L  H  G  N  T  M  E  K  L  I  K  K  R  N  V  P  Q  N  L  S  P  H  S
1607 GGCCTCCTGCATGGAAACACAATGGAGAAGCTGATCAAGAAGAGGAATGTCCCACAGAATCTGTCACCCCATAG 503

Q  R  P  D  I  L  K  A  E  S  L  L  P  K  L  D  A  A  L  S  G  V  G  L
1680 CCAAAGGCCAGATATCCTCAAGGCGGAGTCTTTGCTCCCTAAACTAGATGCAGCCCTGAGTGGGGTGGGGCTT 527

P  G  C  P  K  A  P  P  S  P  G  R  S  R  R  G  K  ▸T  R  H  R  K  A  S
1753 CCTGGGTGTCCAAAGGCCCCATCACCAGGACGCAGTCGGAGACAGGGGGAAGACTCGGCATAGGAAGGCCAGC 551

A  K  G  S  C  G  D  L  P  G  L  R  T  A  V  P  P  H  E  P  G  G  P  G  S
1826 GCCAAGGGCAGCTGTGGAGACCTGCCCGGCCTGCGCACAGCTGTCCCACCCCATGAACCCGGTGGCCCTGGCTCA 576

P  G  G  L  G  G  G  P  S  A  W  E  A  C  P  P  A  L  R  G  L  H  H  D
1899 CCCGGGGGGCTAGGAGGGGGCCCCAGTGCCTGGGAAGCCTGCCCTCCAGCCCTAAGGGGTCTCCATCATGAC 600

L  L  L  R  K  M  S  S  S  P  D  L  L  S  A  A  L  G  S  R  G  R  G
1972 CTCCTGCTCCGAAAAGTCTTCATCGCGATCTCCAGCCCAGACCTGCTGAGCGCTGCCCTGGGCTCCAGGGGGCGAGGC 624

A  T  G  G  A  G  D  P  G  S  P  P  P  A  R  G  D  T  P  P  S  E  G  S  A
2045 GCCACAGGGCGGGAGGCGACCCAGGATCCCCAGATTCACCGGGGACACCCCACCAGTGAGGGGTCTGCA 649

P  G  S  T  S  P  D  S  P  G  G  A  K  G  E  P  P  P  V  G  P  G  E
2118 CCTGGCTCCACCAGCCCTGACAGCCCCGGTGGGGCCAAGGGAGAGCCACCACCTGTGGGTCCAGGACTG 673

G  V  G  L  L  G  T  G  R  E  G  T  S  G  R  G  G  S  R  A  G  S  Q  H
2191 GGTGTGGGCCTTCTTGGGACTGGGGAGGGGAGCAGTGGACGGAGGGGAAAGTCAGGGCATCATTGAAAGGA 697
```

```
        L  T  P  A  A  L  L  Y  R  A  A  V  T  R  S  Q  K  R  G  I  S  S  E  E  E      722
2264    GGAAGGAGAGTAGACAGTAGAAGTAGCTGACATCAGCAGGTGCCTCAGCGTGCTCAGCCTGAACATGGCCAG
          E  G  E  V  D  S  E  V  E  L  T  S  S  Q  R  W  P  Q  S  L  N  M  R  Q      746
2337    TCACTACTACTTCAGCTACAGAATCATCAGAAGAGGAGAGCAGGACCTAGTGAACTTCCCAGTG
            S  L  S  T  F  S  S  E  N  P  S  D  G  E  E  G  T  A  S  E  P  P  S  S    770
2410    GCACCCTGAGTGCCAACCTGAGTCTGATGGCACGGATCAGCCGCCATCAGCCATCATGTCTCCAGG
              G  T  P  E  V  G  S  T  N  T  D  E  R  P  D  E  R  S  D  D  M  C  S  Q  G 795
2483    CTCAGAATCCACCTGAGAGTCTTGAGGTCATCCCGGAGTCATCAGACCACTCCTGCCATTCCA
                S  E  I  P  L  D  P  P  P  S  E  V  I  P  G  P  E  P  S  S  L  P  I  P 819
2556    CACCTGGAACTTCAGAGAGGCCCCTCCAATTCAGAGCTGAGACTGTGACAGCACTGAATTGACA
                  H  Q  E  L  L  R  E  R  G  P  P  N  S  E  D  S  D  C  D  S  T  E  L  D 843
2629    AATCCAACGCGTTACTGCCGTTGCCCTGCCCTCCCATGaagcactcgtattcctgtacta
                    N  S  N  S  V  D  A  L  R  P  P  A  S  L  P  P  *              859
2702    tagagaaatatttatgattatatacatatatatgccacataatcaacagaaaga
2775    tggggctgtcgtccagccgctaagtcaggctcgagggagactgatccctgaccattcacctgataaactctagg
2848    gacactgtgcagctgtgaatgatgaggcacagccgtaaggcaagccctccctgcccc
2921    acccccattccttatattcagcaagcaacaaggcaatagaaaagccaggttgtcttttattcttatccccca
2994    aatatagggggtggggggagggcgtggaggagcgagagaaaccacttagactgcacttttctgttc
3067    cgtttactctgtttacacatttgcacttggagggggaggctaaggctggtcctcccccctgaggttct
3140    caggtggcaatgtaactgtaactcatttttgtcccaagcctgtgcccaagccctgtcttaaggccagg
3213    gggaggttaggagactgatagcatgtgatgctcaggctgaagaaccggggttctgttaagtcctgcttt
3286    atcctgtgcctgattggggtgggactgtcctactgtaaccctgtaaccttgaaaaataactccca
3359    tgcaggaaaaaaaaaaaaaaaaaaaa
```

HUMAN LEUCINE-ZIPPER PROTEIN KINASE AND METHODS OF USE

CROSS REFERENCE TO RELATED APPLICATIONS

This is a continuation in part of U.S. Ser. No. 08/205,018 filed Mar. 1, 1994, the contents of which are incorporated by reference herein in their entirety.

REFERENCE TO GOVERNMENT GRANTS

The work present herein was supported in part by National Institute of Health grants NS08075, NS25044 and NS31102. The United States government may have certain rights in the invention.

FIELD OF THE INVENTION

This invention is directed to a novel protein-kinase, nucleic acid sequences encoding the same and methods related thereto.

BACKGROUND OF THE INVENTION

Protein kinases regulate various cellular responses to changing environmental conditions. Protein kinases fall into two general classes: those protein kinases that transfer phosphate to serine or threonine and those proteins that transfer phosphate to tyrosine (Krebs and Beavo, *Annu. Rev. Biochem* 48: 923–959 (1979)). A few protein kinases, such as weel, now appear to be capable of phosphorylating both ser/threonine and tyrosine (Lindberg et al., *Trends Biochem Sci* 17: 114–119 (1992)). Phosphorylation is of particular significance in controlling mitogenesis and cellular differentiation. Receptors for a number of polypeptide growth factors are transmembrane tyrosine kinases (Yarden and Ullrich, *Annu. Rev. Biochem* 57: 443–478 (1988)), which in turn stimulate serine/threonine kinases such as protein kinase C, MAP kinase and p74$^{raf}$ (Hunter et al., *Nature* 311: 480–483 (1984); Morrison et al., *Cell* 58: 649–657 (1989); Rossomondo et al., *Proc. Natl. Acad. Sci. USA* 86: 694–6943 (1989)).

Protein kinases, and especially the overexpression thereof, have been found to be linked to hyperproliferation of cells and metastasis. Many protein kinases were first identified as the products of oncogenes and still constitute the largest family of known oncogenes. Lindberg and Hunter, *Mol. and Cell. Biol.*, 10(11): 6316–6324 (1990).

Mutations of genes encoding members of the protein kinase family which are involved in the regulation of neuroblastic proliferation, differentiation and survival play a role in the etiology of human central nervous system tumors. Thus, it is highly desirable to gain a greater understanding of this class of proteins, as well as to use such greater understanding to limit or inhibit the effects that these proteins have on cellular hyperproliferation.

SUMMARY OF THE INVENTION

There is provided by the present invention a cDNA sequence encoding a novel protein kinase, leucine-zipper protein kinase (zpk), and the protein encoded thereby.

There are provided by the present invention recombinant constructs encoding leucine-zipper protein kinase.

There are provided by the present invention novel methods of use and diagnosis for leucine-zipper protein kinase and cDNA coding for leucine-zipper protein kinase.

DETAILED DESCRIPTION OF THE INVENTION

A novel member of the protein serine/threonine kinase family, leucine-zipper protein kinase is provided by the present invention. As used herein, the term leucine-zipper protein kinase (zpk) refers to a protein having an amino acid sequence substantially homologous to at least a portion of the amino acid sequence set forth in SEQ ID NO: 2. In accordance with the present invention, the term "homologous" refers to a one to one correlation between the sequences of two polypeptides or oligonucleotides. Of course, 100% homology is not required in all cases. In some instances polypeptides of the present invention may be substantially homologous to the amino acid sequence set forth in SEQ ID NO: 2. Substantial homology requires only that the essential nature of the polypeptide, i.e. folding characteristics and unique features such as the leucine zipper are preserved. Thus, modifications of the leucine-zipper protein kinase are anticipated and are within the scope of the present invention. These modification may be deliberate, as through site directed mutagenesis, or may be accidental as through mutations in host which are producers of the protein. In some embodiments of the present invention polypeptides of the present invention may be at least about 75% homologous to the sequence set forth in SEQ ID NO: 2. In other embodiments of the present invention polypeptides may be at least about 85% homologous to the sequence set forth in SEQ ID NO: 2. In yet other embodiments of the present invention polypeptides may be at least about 95% homologous to the sequence set forth in SEQ ID NO: 2. It is also anticipated that certain non-commonly occurring amino acids may be substituted for commonly occurring counterparts to confer desirable characteristics to the resulting polypeptide.

Furthermore, it is contemplated in some aspects of the present invention that a polypeptide may comprise only a portion of the sequence set forth in SEQ ID NO: 2. This may be the case, for example, for a chimeric protein encompassing active or otherwise desirable portions of a number of proteins. A portion may also refer to a truncated polypeptide, be it substantially truncated or only slightly truncated. Such truncated polypeptides may be the result of an idiosyncracy in the mode of production which results in truncation of amino acids from a terminal end, or a finding that the truncated polypeptide works as well or better than the full-length protein. For example, it might be found that the region directly surrounding the protein kinase domain at amino acids 231–243 is especially active.

Of course, in still other aspects of the present invention, the full-length protein, as set forth in SEQ ID NO: 2, is contemplated.

The leucine-zipper protein kinase of the present invention, depending on the pH of its environment, if suspended or in solution, or of its environment when crystallized or precipitated, if in solid form, may be in the form of pharmaceutically acceptable salts or may be in neutral form. The free amino acid groups of the protein are, of course, capable of forming acid addition salts with, for example, organic acids such as hydrochloric, phosphoric, or sulfuric acid; or with organic acids such as, for example, acetic, glycolic, succinic, or mandelic acid. The free carboxyl groups are capable of forming salts with bases, including inorganic bases such as sodium, potassium, or calcium hydroxides, and such organic bases as piperidine, glucosamine, trimethylamine, choline, and caffeine. In addition, the protein may be modified by combination with other biological materials such as lipids and saccharides, or by side chain modifications such as acetylation of amino groups, phosphorylation of hydroxyl side chains or oxidation of sulfhydryl groups.

The leucine-zipper protein kinase is preferably purified and isolated. "Purified" and "isolated" as the terms are used herein, are meant to refer to molecules which have been purified or synthesized so as to be substantially homogenous. The terms do not exclude the possibility that certain impurities may be present in the composition as long as the essential nature of the protein is intact.

Figure 1A:
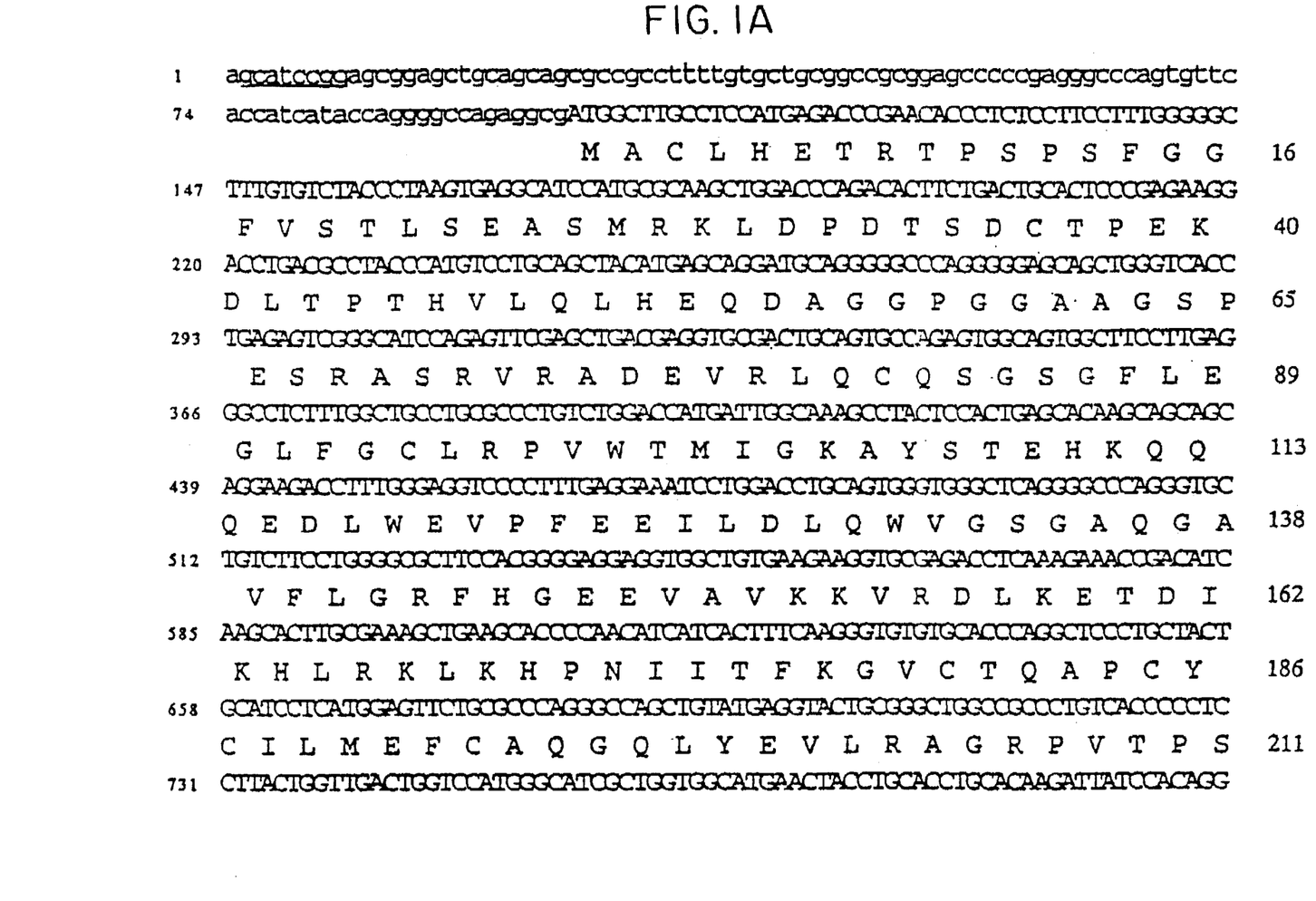
FIGS. 1A, 1B, 1C and 1D. Nucleotide sequence (SEQ ID NO: 1) and putative amino acid sequence (SEQ ID NO: 2) of leucine-zipper protein kinase. Amino acid numbering starts with the initiation codon.
Figure 1B:
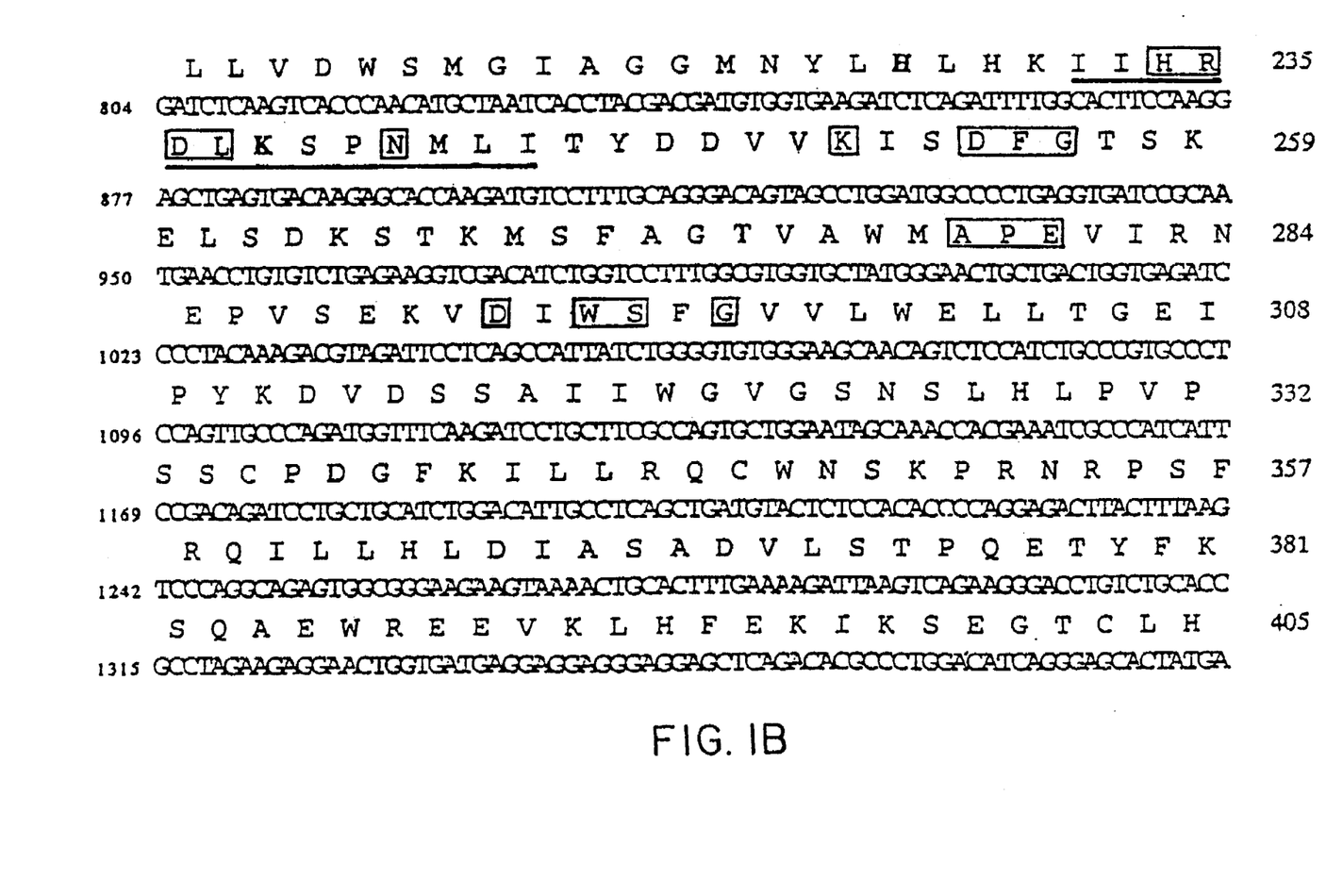
Figure 1C:
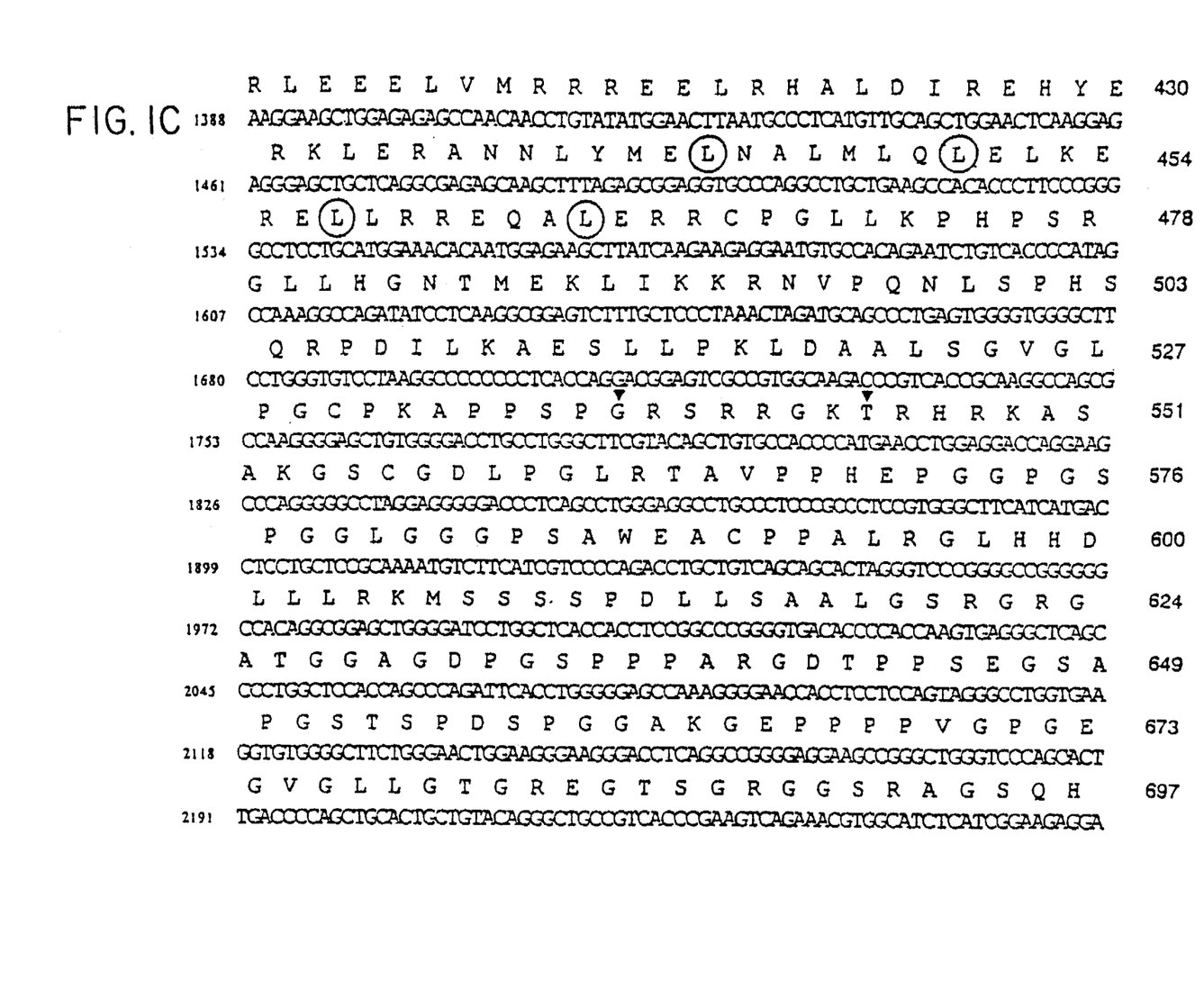
Figure 1D:
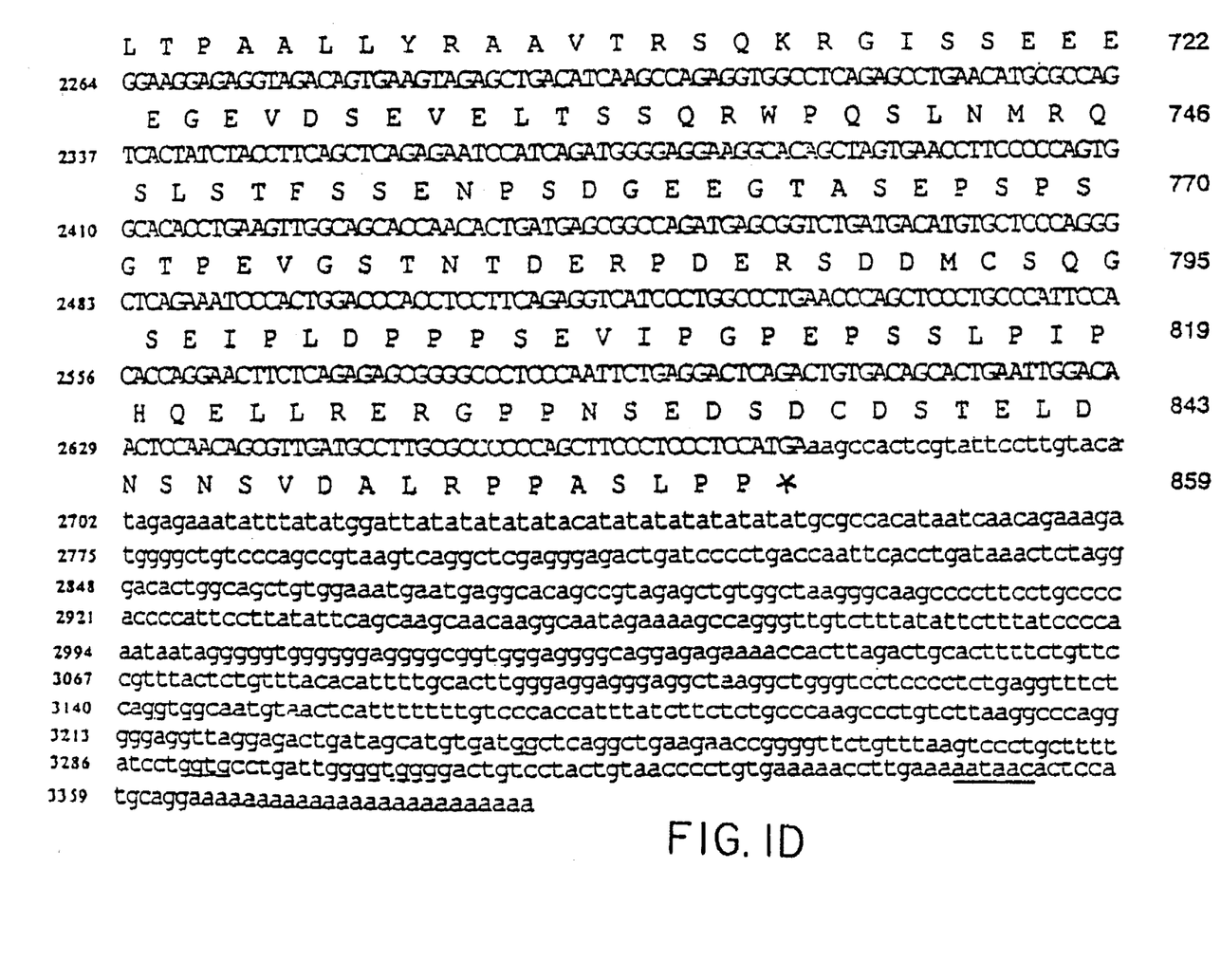
Figure 2A:
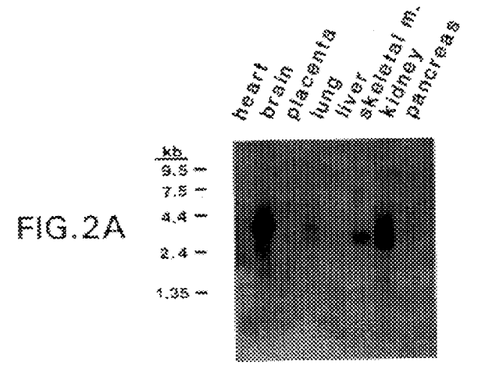
FIGS. 2A, 2B, 2C and 2D. Northern blots of expression of leucine zipper protein kinase in human tissue. Panel A represents Northern blots hybridized to $\alpha$-[$_{32}$P] labeled leucine zipper protein kinase cDNA from human adult tissue FIG. 2A and from human fetal tissue FIG. 2C. Panel B represents Northern blots hybridized to $\alpha$-[$_{32}$P] labeled $\beta$-actin cDNA from human adult tissue FIG. 2B and from human fetal tissue FIG. 2D.
Figure 2B:
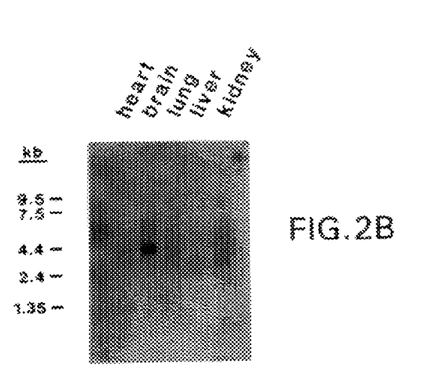
Figure 2C:
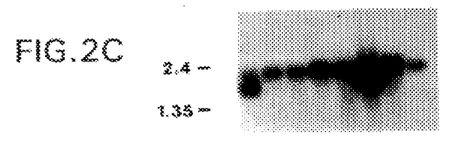
Figure 2D:
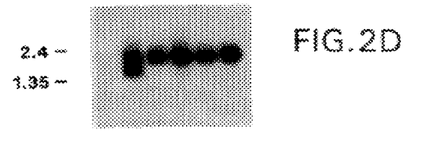

Tissue distribution analysis indicated that leucine-zipper protein kinase is present in the brain, more so in the adult than in the fetal brain based upon the detection of a 3.4 Kb mRNA transcript. A smaller mRNA transcript, about 3.2 Kb was detected in kidney and skeletal muscle. Adult lung tissue expressed both transcripts at a very low level. In fetal tissue, the only definite transcript seen is in the brain. These results can be seen in FIGS. 2A, 2B, 2C and 2D.

The cDNA sequence of a novel leucine-zipper protein kinase is also provided by the present invention. The cDNA has a long open reading frame encoding 859 amino acids. The methionine codon at nucleotides 99–101 matches Kozak's consensus sequence for the initiation of translation. Kozak *Nucleic Acid Res* 9: 5233–5252 (1981). The polyadenylation signal AATAAC was found at nucleotides 3347–3352. Wickens and Stephenson, *Science* 226: 1045–1051 (1984). The 5' cap site is CATCCG, 90 base pairs from the initiation start site.

Homology searches of leucine-zipper protein kinase with the nucleotide and amino acid databases showed no homology to any known protein kinase family. Leucine-zipper protein kinase is most similar to serine/threonine specific protein kinases. The leucine zipper protein kinase protein is believed to be a "non-receptor type kinase" based on its lack of a transmembrane domain. The consensus sequences for the ATP-binding site, Gly-Xaa-Gly-Xaa-Xaa-Gly and Lys residues are found at positions 537–544 and 548, respectively. The protein kinase domain was found to be at position 231–243. Taylor, et al., *Annu. Rev. Cell Biol.*, 8, 429–462 (1992). Two overlapping sites of leucine zipper motif (leucine at every seventh amino acid) occur at position 442–468. A putative endoplasmic reticulum-targeting sequence was located at residues 415–418 (Pelham, H.R.B., *Annu. Rev. Cell Biol.*, 5, 1–23 (1989).

Comparison with other members of the family of protein kinases indicate that leucine-zipper protein kinase has a number of novel features. First, the glycine rich loop in leucine zipper protein kinase is present towards the C-terminus of the catalytic domain, whereas in other protein kinases it is present near the N-terminus.

Endoplasmic reticulum targeting sequences (REEL) have been identified in both soluble; Pelham, H.R.B., *Annu. Rev. Cell. Biol.*, 5, 1–23 (1989); and transmembrane; Jackson, et al., *EMBO J.*, 9, 3153–3162 (1990) endoplasmic reticulum proteins. A lysine rich motif at the cytoplasmically-exposed C-terminus of some transmembrane proteins was described which conferred endoplasmic reticulum localization, although a more complex retention signal at the C-terminus has also be postulated. Gabathuler and Kvist, *J. Cell Biol.*, 111, 1803–1810 (1990). Leucine-zipper protein kinase contains an endoplasmic reticulum targeting sequence which is located from amino acid 415–416, rather than at the extreme C-terminus of the protein.

Leucine-zipper protein kinase is also unique in that it contains a leucine-zipper motif, a sequence in which leucines occur at every seventh amino acid. Leucine-zippers contribute to targeting of various proteins (eg. glucose transporters, Asano, et al., *J. Biol. Chem.*, 267, 19636–19641 (1992)) and permit dimerization of various cytoplasmic hormone receptors and enzymes. Forman, et al., *Mol Endocrinol*, 3, 1610–1626 (1989). Leucine zippers are also a common feature of protein transcription factors, where they permit homo- or heterodimerization resulting in tight binding to DNA strands.

A leucine-zipper motif has been reported only once previously in a protein kinase, the bovine cGMP-dependent protein kinase, which has a leucine-isoleucine zipper motif at its N-terminus. Wernet, et al., *FEBS*, 251, 191–196 (1989).

Leucine-zipper protein kinase can be routinely synthesized in substantially pure form by standard techniques well known in the art, such as commercially available peptide synthesizers and the like.

Additionally, leucine-zipper protein kinase can be efficiently prepared using any of numerous well known recombinant techniques such as those described in U.S. Pat. No. 4,677,063 which patent is incorporated by reference as if fully set forth herein. Briefly, most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides additional markers which can be either retained or destroyed in constructing the desired vector. Commonly used procaryotic control sequences include promoters for transcription initiation, optionally with an operator, along with ribosome binding site sequences, include such commonly used promoters as the beta-lactamase (penicillinase) and lactose (lac) promoter systems (Chang, et al., *Nature* (1977) 198:1056) and the tryptophan (trp) promoter system (Goeddel, et al. *Nucleic Acids Res* (1980) 8:4057) and the lambda derived $P_L$ promoter and N-gene ribosome binding site (Shimatake, et al., *Nature* (1981) 292:128).

In addition to bacteria, eucaryotic microbes, such as yeast, may also be used as hosts. Laboratory strains of *Saccharomyces cerevisiae*, Baker's yeast, are most used although a number of other strains are commonly available. While vectors employing the 2 micron origin of replication are illustrated, Broach, J. R., *Meth Enz* (1983) 101:307, other plasmid vectors suitable for yeast expression are known (see, for example, Stinchcomb, et al., *Nature* (1979) 282:39, Tschempe, et al., *Gene* (1980)10:157 and Clark, L., et al., *Meth Enz* (1983) 101:300). Control sequences for yeast vectors include promoters for the synthesis of glycolytic enzymes (Hess, et al., *J Adv Enzyme Reg* (1968) 7:149; Holland, et al. *Biochemistry* (1978) 17:4900). Additional promoters known in the art include the promoter for 3-phosphoglycerate kinase (Hitzeman, et al., *J Biol Chem* (1980) 255:2073), and those for other glycolytic enzymes such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions are the promoter regions for alcohol dehydrogenase 2, isocytochrome C, acidphosphatase, degradative enzymes associated with nitrogen metabolism, and enzymes responsible for maltose and galactose utilization (Holland, ibid). It is also believed terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M.J., et al., *J Biol Chem* (1981) 256:1385) or the LEU2 gene obtained from YEp13 (Broach, J., et al., *Gene* (1978) 8:121), however any vector containing a yeast compatible promoter, origin of replication and other control sequences is suitable.

It is also, of course, possible to express genes encoding polypeptides in eucaryotic host cell cultures derived from multicellular organisms. See, for example, *Tissue Cultures*, Academic Press, Cruz and Patterson, editors (1973). Useful host cell lines include VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) Fiers, et al., *Nature* (1978) 273:113), or other viral promoters such as those derived from polyoma, Adenovirus 2, bovine papilloma virus, or avian sarcoma viruses. General aspects of mammalian cell host system transformations have been described e.g. by Axel; U.S. Pat. No. 4,399,216. It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes. Plant cells are also now available as hosts, and control sequences compatible with plant cells such as the nopaline synthase promoter and polyadenylation signal sequences (Depicker, A., et al., *J Mol Appl Gen* (1982) 1:561) are available.

Depending on the host cell used, transformation is done using standard techniques appropriate to such cells. The calcium treatment employing calcium chloride, as described by Cohen, S.N., *Proc Natl Acad Sci (USA)* (1972) 69:2110, or methods described in *Molecular Cloning: A Laboratory Manual* (1988) Cold Spring Harbor Press, could be used for procaryotes or other cells which contain substantial cell wall barriers. Infection with *Agrobacterium tumefaciens* (Shaw, C. H., et al., *Gene* (1983) 23:315) is believed useful for certain plant cells. For mammalian cells without such cell walls, the calcium phosphate precipitation method of Graham and van der Eb, *Virology* (1978) 52:546 can be used. Transformations into yeast can be carried out according to the method of Van Solingen, P., et al., *J Bact* (1977) 130:946 and Hsiao, C. L., et al., *Proc Natl Acad Sci (USA)* (1979) 76:3829.

cDNA or genomic libraries can be screened using the colony hybridization procedure. Generally, each microtiter plate is replicated onto duplicate nitrocellulose filter papers (S&S type BA-85) and colonies are allowed to grow at 37° C. for 14–16 hr on L agar containing 50 µg/ml Amp. The colonies are lysed and DNA fixed to the filter by sequential treatment for 5 min with 500 mM NaOH, 1.5M NaCl, and are washed twice for 5 min each time with 5× standard saline citrate (SSC). Filters are air dried and baked at 80° C. for 2 hr. The duplicate filters are prehybridized at 42° C. for 6–8 hr with 10 ml per filter of DNA hybridization buffer (5×SSC, pH 7.0 5x Denhardt's solution (polyvinylpyrrolidine, plus Ficoll and bovine serum albumin; 1×=0.02% of each), 50 mM sodium phosphate buffer at pH 7.0, 0.2% SDS, 20 µg/ml Poly U, and 50 µg/ml denatured salmon sperm DNA).

The samples can be hybridized with kinased probe under conditions which depend on the stringency desired. Typical moderately stringent conditions employ a temperature of 42° C. for 24–36 hr with 1–5 ml/filter of DNA hybridization buffer containing probe. For higher stringencies high temperatures and shorter times are employed. Generally, the filters are washed four times for 30 min each time at 37° C. with 2×SSC, 0.2% SDS and 50 mM sodium phosphate buffer at pH 7, then are washed twice with 2×SSC and 0.2% SDS, air dried, and are autoradiographed at −70° C. for 2 to 3 days.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage can be performed by treating the DNA with a suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by one unit of enzyme in about 20 µl of buffer solution. Incubation times of about one hour to two hours at about 37° C. are workable, although variations can be tolerated. After each incubation, protein can be removed by extraction with phenol/chloroform, and may be followed by ether extraction, and the nucleic acid recovered from aqueous fractions by precipitation with ethanol followed by running over a Sephadex G-5 spin column. If desired, size separation of the cleaved fragments may be performed by polyacrylamide gel or agarose gel electrophoresis using standard techniques. A general description of size separations can be found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 5–10 µM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides can be prepared by the triester method of Metteucci, et al. (*J Am Chem Soc* (1981) 103:3185) or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM MgCl$_2$, 5 mM dithiothreitol, 1–2 Mm ATP, 1.7 pmoles $\gamma^{32}$P-ATP (2,9 mCi/mmole), 0.1 mM spermidine, 0.1 mM EDTA.

Ligations can be performed in 15–30 μl volumes under the following standard conditions and temperatures: 20 mM Tris-Cl pH 7.5, 10 mM MgCl$_2$, 10 mM DTT, 33 μg/ml GSA, 10 mM-50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10—30 fold molar excess of linkers) are performed at 1 μM total ends concentration.

In vector construction employing "vector fragments", the vector fragment can be treated with bacterial alkaline phosphatase (BAP) in order to remove the 5' phosphate and prevent religation of the vector. BAP digestions can be conducted at pH 8 in approximately 150 mM Tris, in the presence of Na+ and Mg+$^2$ using about 1 unit of BAP per μg of vector at 60° C. for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis can be used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques can be hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Correct ligations for plasmid construction can be confirmed by first transforming a suitable host with the ligation mixture. Successful transformants are selected by ampicillin, tetracycline or other antibiotic resistance or using other markers depending on the mode of plasmid construction, as is understood in the art. Plasmids from the transformants can then be prepared according to the method of Clewell, D.B., et al. *Proc Natl Acad Sci (USA)* (1969) 62:1159, optionally following chloramphenicol amplification (Clewell, D.B., *J Bacteriol* (1972) 110:667). The isolated DNA Is analyzed by restriction and/or sequenced by the dideoxy method of Sanger, F., et al. *Proc Natl Acad Sci (USA)* (1977) 74:5463 as further described by Messing, et al., F. Supp. *Nucleic Acids Res* (1981) 9.309, or by the method of Maxam, et al., *Methods in Enzymology* (1980) 65:499.

In accordance with the present invention polynucleotide probes specifically hybridizable to a portion of the leucine zipper protein kinase gene are provided. Polynucleotide probes substantially homologous to a portion of the leucine-zipper protein kinase gene are also provided. Such probes may be used for diagnostic or research purposes to detect or quantitate the expression of leucine zipper protein kinase in a sample such as by detecting the presence or absence of polynucleotide duplex formation between the polynucleotide probe and leucine-zipper protein kinase gene. Samples may derived from cell culture or may be derived from a patient. Samples may be biological fluids such as synovial fluid in some aspects of the invention. Tissue samples may also be used in some embodiments of the present invention. Detection of the presence of polynucleotide duplexes is indicative of the presence of the leucine-zipper protein kinase gene in a sample and may be indicative of diseases associated with leucine zipper protein kinase, such as tumors of the central nervous system. Provision of means for detecting hybridization of polynucleotides with the leucine-zipper protein kinase gene can routinely be accomplished. Such provision may include enzyme conjugation, radiolabelling or any other suitable detection systems. Kits for detecting the presence or absence of leucine zipper protein kinase or a particular transcript thereof may also be prepared. Said polynucleotide probes may range in length from about 5 to about 100 nucleotide units. In more preferred embodiments of the present invention the probes may be from about 8 to about 75 nucleotide units in length. Ideally, said probes range in length from about 12 to about 50 nucleotide units. It is recognized that since polynucleotide probes of the present invention may preferably not exceed 100 nucleotides in length, said probes may specifically hybridize to only a portion of the targeted sequence. The portion of the leucine zipper protein kinase sequence to be targeted can be identified by one skilled in the art. Most suitably, a target sequence is chosen which is unique, thereby decreasing background noise attributable to hybridization by the probe other than to the target. By way of example, one skilled in the art would be unlikely to select a repeating sequence of adenine nucleotide units as this is a common sequence occurring in many genes. The practitioner might choose to perform a search and comparison of sequences found in a sequence repository such as Genbank in order to identify and design a useful probe. Such methods of conventionally used to identify unique sequences. These unique sequences, when used as probes, need not necessarily be crucial to the regulation of the expression of leucine-zipper protein kinase.

In accordance with other methods of the present invention, neuronal cells may be contacted with leucine-zipper protein kinase, or a portion thereof in order to inhibit cellular proliferation. While not wishing to be bound to a particular theory, it is believed that the addition of exogenous leucine-zipper protein kinase, or portions thereof may interfere with specific protein-protein or protein-nucleic acid interactions involved in cellular hyperproliferation. For example, by administering an inactive leucine-zipper protein kinase polypeptide or a portion thereof, it may be possible to compete with naturally occurring leucine-zipper protein kinase for binding regions of target nucleic acid molecules or polypeptides in order to modulate its effect in the cell at the level of protein-protein or protein-nucleic acid interactions. In this way, it may be possible to treat a mammal suffering from tumors of the central nervous system by inhibiting the overexpression of leucine-zipper protein kinase in vivo or by interfering with a vital signal in the chain of signals leading to tumorigenicity.

For methods of the present invention, leucine-zipper protein kinase may be formulated into pharmacological compositions containing an effective amount of leucine-zipper protein kinase and a usual nontoxic carrier, such carriers being known to those skilled in the art. The compositions may be administered by a method suited to the form of the composition. Such compositions are, for example, in the form of usual liquid preparations including solutions, suspensions, emulsions, and the like which can be given orally, intravenously, subcutaneously or intramuscularly.

The present invention is also directed to methods of inhibiting hyperproliferation of neuronal cells comprising contacting the cells with oligonucleotides substantially complementary to a portion of the nucleic acid sequence set forth in SEQ ID NO: 1. "Complementary" in the context of this invention, means the ability to form hydrogen bonds, also known as Watson-Crick base pairing, between complementary bases, usually on opposite nucleic acid strands or two regions of a nucleic acid strand, to form a double-stranded duplex. Guanine and cytosine are examples of complementary bases which are known to form three hydrogen bonds between them. Adenine and thymine are examples of complementary bases which are known to form two hydrogen bonds between them. "Specifically hybridizable" and "substantially complementary" are terms which indicate a sufficient degree of complementarity to avoid non-specific binding of the oligonucleotide (or polynucleotide probe) to non-target sequences under conditions in which specific binding is desired, i.e., under physiological conditions in the case of in vivo assays and therapeutic treatment, or, in the case of in vitro assays, under conditions in which the assays are conducted. It is understood that an oligonucleotide, polynucleotide probe or nucleic acid sequence need not be 100% complementary to its target nucleic acid sequence to be specifically hybridizable or effective in methods of the present invention. Thus, in some embodiments of the present invention about 50% homology is envisioned. About 75% percent homology is preferred in some aspects of the present invention and about 80% homology is still more preferred. Ninety percent homology may be preferred in yet other embodiments of the present invention. In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. The oligonucleotides in accordance with this invention preferably comprise from about 5 to about 50 nucleotide units. It is more preferred that such oligonucleotides comprise from about 8 to 30 nucleotide units, and still more preferred to have from about 12 to 25 nucleotide units.

Oligonucleotides of the present invention may be prepared by standard techniques such as solid-phase synthesis which are well known to those skilled in the art.

Furthermore, in accordance with methods of the present invention, a therapeutically effective amount of oligonucleotide is administered to a mammal suffering from tumors of the central nervous system.

Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotides.

The pharmaceutical compositions of the present invention may be administered in a number of ways depending on whether local or systemic treatment is desired, and on the area to be treated. Administration may be done topically (including ophthalmically, vaginally, rectally, intranasally), orally, by inhalation, or parenterally, for example by intravenous drip or subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms or gloves may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The following examples are illustrative and are not meant to be limiting of the present invention.

EXAMPLES

Example 1

Cells

Human teratocarcinoma line NT2 was differentiated into postmitotic neurons NT2-N with retinoic acid as previously described (Pleasure et al., *J. Neurosci* 12: 1802–1815 (1992); Younkin et al., *Proc. Natl. Acad. Sci. USA* 90: 2174–2178 (1992)). Poly(A)$^+$ RNA was isolated from both NT2 and NT2-N neurons using Invitrogen mRNA kit.

Example 2

Subtractive Hybridization and DNA Amplification

Invitrogen's Subtractor probe kit was used according to the manufacturer's instructions to isolate two different subtracted cDNAs UND and DIFF. UND was enriched in transcripts expressed in the undifferentiated stage whereas DIFF was enriched in transcripts present in the neurons. One µg portions of UND and DIFF mRNA were used for PCT amplification with degenerate primers as described in Wilks *Proc. Natl. Acad. Sci. USA* 86: 1603–1607 (1989). PCT was performed using a Geneamp kit (Cetus) with 1 μg of each of the degenerate primers. The final concentration of magnesium was 2.1 mM. PCR cycling was performed on a Perkin-Elmer 480 thermal cycler for 39 cycles with a profile of 1.3 minutes at 95° C. (denaturation), 2 minutes at 45° C. (annealing), and 2 minutes at 64° C. (elongation).

Example 3

Subcloning of Amplified DNAs and DNA Sequencing

The PCR reaction mixture were run on 4% Nusieve agarose gel and the amplified band of ~220 bp was excised. The band was purified using Magic PCR Kit (Promega). The amplified DNA was digested with the restriction enzymes BamH1/EcoR1. The amplified DNAs were subcloned into the BamH1 and EcoR1 cleaved Bluescript DNA. A total of about 200 clones (100 representing UND and 100 representing DIFF) were examined by sequencing using a Taq DyeDeoxy terminator cycle sequencing kit (Applied Biosystems). Plasmid DNA was isolated using Qiagen column 20. The cycle sequencing reactions were performed in a Perkin-Elmer 480 thermal cycler for 25 cycles with a profile of 96° C. for 30 seconds, 40° C. for 15 seconds, and 60° C. for 4 minutes. Following separation of the extension products on a Select-D G-50 column (5 Prime 3 Prime) the reaction mixtures were dried, resuspended in 4 μl of 5:1 formamide/50 mM EDTA, loaded on a 6% sequencing gel, and analyzed using an Applied Biosystems 373 fluorescent sequencer.

Example 4 cDNA Library Screening

The 210 bp 10.2 PCR clone from undifferentiated clones was radiolabelled with [$^{32}$P] dCTP and used to probe ~$10^6$ plaques from an amplified human fetal brain library (Stratagene) to obtain larger cDNA clones. Hybridization was carried out overnight at 42° C. in 50% Formamide, 5×SSPE, 5×Denhardt's , 1% SDS, 100 ug/ml sheared salmon sperm DNA, and 1×$10^6$ cpm/ml of probe. Filters were washed at 60° C. twice in 2×SSC containing 0.1% SDS, and exposed overnight to Kodak XAR-5 film at -70° C.

Example 5

Sequence Determination cDNAs were subcloned into a plasmid vector BluescriptSk. For complete sequence determination, unidirectional nested deletions was performed using the Exo111/ Mung Bean nuclease kit from Stratagene. The colonies obtained after deletions were sequenced as described earlier using a Tag DyeDeoxy terminator cycle sequencing kit (Applied Biosystems). The DNA sequence obtained was determined after sequencing twice.

Example 6

Sequence comparisons

All sequence manipulations were done on a VAX using the University of Wisconsin Genetics Computer Group Sequence Analysis Software Package. DNA fragments obtained after nested deletions was assembled into Contigs using the Programme Sequencer 2.0 (Gene Codes Corp). Protein analysis was done using MacVector (IBI).

Example 7

RNA Analysis

Human multiple tissue northern blots were purchased from Clontech laboratories. Hybridization conditions were similar to that used for library screening. Filters were washed to a final stringency of 0.1×SSC/0.1% SDS at 65° C. before exposure to XAR-5 x-ray film.

Example 8

Localization of the zpk Gene to Chromosome 12

Fluorescence in situ hybridization (FISH) and somatic cell hybrid analysis were used to localize the zpk gene to chromosome 12 of the human genome. Briefly, a zpk clone, ZPK P1, was obtained using two oligonucleotides CCATGAAAGCCACTCGTATTCCT (SEQ ID NO: 3) and TCTTTCTGTTGATTATGTGGCGC (SEQ ID NO: 4), both of which correspond to the 3' untranslated region. This clone, ZPK P1, was shown to contain the zpk sequence by digesting the plasmid with EcoR1 and HindIII and by Southern analysis with [α-$^{32}$P]-labeled ZPK cDNA.

To map the zpk gene, FISH and somatic cell hybrid analysis were performed. The ZPK P1 clone was labeled by nick-translation with digoxigenin-11-dUTP using a large fragment labeling kit from Oncor (Gaithersburg, MD). Human metaphase chromosome spreads were prepared from phytohemagglutinin-stimulated peripheral blood lymphocytes from normal controls according to routine methods. Labeled ZPK (200 ng) and Cot-1 DNA (20 μg) were dissolved in 15 μl of Hybrisol VII (Oncor), denatured for 5 minutes at 70° C., preannealed at 37° C. for 30 minutes, and applied to slides that had been denatured at 70° C. for 2 minutes. The slides were hybridized overnight at 37° C. and then rinsed at 39° C. in 50% formamide/1×SSC for 10 minutes, followed by two washes in 2×SSC for 2 minutes each. Detection of probes was accomplished with anti-digoxigen rhodamine (Oncor). Cells were counterstained with DAPI/antifade (Oncor) and viewed with a Zeiss axiophot microscope equipped with a triple band pass filter set. A total of 50 metaphase cells were examined in replicate experiments and demonstrated signals on one or both chromatids for both chromosomes 12 in all metaphases examined.

To confirm independently the map location for zpk to chromosome 12, ZPK cDNA was hybridized to a somatic cell hybrid mapping panel. The panel consisted of the following cell lines and chromosomal number (in parenthesis): GM10880 (1, 3, 14); GM10826B (2); GM10253 (3); GM10115 (4); GM10114 (5); GM10629 (6); GM10791 (7); GM10156B (8); GM10611 (9); GM10926B (10); GM10927A9 (11); GM10868 (12); GM10898 (13); GM10479 (14); GM11418 (15); GM10567 (16); GM10498 (17); GM11010 (18); GM10612 (19); GM10478 (4,20); GM08854 (21); GM10888 (22); PHL-17 (X); and GM06317 (Y). The mouse cell line Cl 1-D and chinese hamster cell line RJK-88 were used as rodent controls.

Ten micrograms of DNA from each cell line was digested with HindIII, loaded onto a 0.8% agarose gel, subjected to electrophoresis, and blotted onto Hybond-N (Amersham). The ZPK cDNA probe was labeled by the random primer method with [α-$^{32}$] and hybridized overnight at 68° C. in Church's solution (1 mM EDTA, 7% SDS, 0.5 M sodium phosphate, pH 7.2). Blots were washed for one hour in 2×SSC/0.1% SDS at 68° C. and exposed to radiography film for 48 hours. Two bands corresponding to those seen on Southern blots from normal human genomic DNA were observed in GM10868, which contains chromosome 12 as the only human chromosome, confirming that the human zpk gene maps to chromosome 12.

What is claimed is:

1. A substantially purified, isolated human leucine-zipper protein kinase.

2. A purified human leucine zipper protein kinase produced from cDNA having a sequence at least 85% homologous to the nucleic acid sequence set forth in SEQ ID NO: 1.

3. A substantially purified, isolated human leucine-zipper protein kinase comprising a protein having a sequence at least about 85% homologous to the amino acid sequence set forth in SEQ ID NO: 2.

4. A pharmaceutical composition comprising leucine-zipper protein kinase in a pharmaceutically acceptable carrier.

5. A method of inhibiting the formation of protein-protein kinase complexes in a cell comprising contacting said cell with polypeptides having a sequence at least 85% homologous to the sequence set forth in SEQ ID NO: 2.

6. A method of inhibiting the formation of nucleic acid-protein kinase complexes in a cell comprising contacting said cell with polypeptides having a sequence at least 85% homologous to the sequence set forth in SEQ ID NO: 2.

7. A method of treating a mammal suffering from tumors of the central nervous system comprising administering to said mammal a therapeutically effective amount of a polypeptide having a sequence at least 85% homologous to the sequence set forth in SEQ ID NO: 2.

8. A method of inhibiting the formation of protein-protein kinase complexes in a cell comprising contacting said cell with polypeptide having a sequence at least 85% homologous to a portion of the sequence set forth in SEQ ID NO: 2, said portion comprising at least amino acids 442–468.

9. A method of inhibiting the formation of nucleic acid-protein kinase complexes in a cell comprising contacting said cell with polypeptide having a sequence at least 85% homologous to a portion of the sequence set forth in SEQ ID NO: 2, said portion comprising at least amino acids 442–468.

10. A method of treating a mammal suffering from tumors of the central nervous system comprising administering to said mammal a therapeutically effective amount of polypeptide having a sequence at least 85% homologous to a portion of the sequence set forth in SEQ ID NO: 2, said portion comprising at least amino acids 442–468.

* * * * *

UNITED STATES PATENT AND TRADEMARK OFFICE
CERTIFICATE OF CORRECTION

PATENT NO. : 5,676,945
DATED : October 14, 1997
INVENTOR(S) : Usharani Reddy and David Pleasure It is certified that error appears in the above-identified patent and that said Letters Patent is hereby corrected as shown below:

Col. 1, line 38, "694-6943" should be --6940-6943--.

Col. 25, line 18, after "comprising" insert --human--.

Signed and Sealed this

Third Day of February, 1998

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 3389 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 99..2105

( x i ) SEQUENCE DESCRIPTION: SEQ ID NO:1:

```
AGCATCCGGA  GCGGAGCTGC  AGCAGCGCCG  CCTTTTGTGC  TGCGGCCGCG  GAGCCCCGA     60

GGGCCCAGTG  TTCACCATCA  TACCAGGGGC  CAGAGGCG  ATG GCT TGC CTC CAT         113
                                              Met Ala Cys Leu His
                                               1               5

GAG ACC CGA ACA CCC TCT CCT TCC TTT GGG GGC TTT GTG TCT ACC CTA           161
Glu Thr Arg Thr Pro Ser Pro Ser Phe Gly Gly Phe Val Ser Thr Leu
             10                  15                  20

AGT GAG GCA TCC ATG CGC AAG CTG GAC CCA GAC ACT TCT GAC TGC ACT           209
Ser Glu Ala Ser Met Arg Lys Leu Asp Pro Asp Thr Ser Asp Cys Thr
                 25                  30                  35

CCC GAG AAG GAC CTG ACG CCT ACC CAT GTC CTG CAG CTA CAT GAG CAG           257
Pro Glu Lys Asp Leu Thr Pro Thr His Val Leu Gln Leu His Glu Gln
             40                  45                  50

GAT GCA GGG GGC CCA GGG GGA GCA GCT GGG TCA CCT GAG AGT CGG GCA           305
Asp Ala Gly Gly Pro Gly Gly Ala Ala Gly Ser Pro Glu Ser Arg Ala
         55                  60                  65

TCC AGA GTT CGA GCT GAC GAG GTG CGA CTG CAG TGC CAG AGT GGC AGT           353
Ser Arg Val Arg Ala Asp Glu Val Arg Leu Gln Cys Gln Ser Gly Ser
 70                  75                  80                  85

GGC TTC CTT GAG GGC CTC TTT GGC TGC CTG CGC CCT GTC TGG ACC ATG           401
Gly Phe Leu Glu Gly Leu Phe Gly Cys Leu Arg Pro Val Trp Thr Met
                 90                  95                 100

ATT GGC AAA GCC TAC TCC ACT GAG CAC AAG CAG CAG CAG GAA GAC CTT           449
Ile Gly Lys Ala Tyr Ser Thr Glu His Lys Gln Gln Gln Glu Asp Leu
                105                 110                 115

TGG GAG GTC CCC TTT GAG GAA ATC CTG GAC CTG CAG TGG GTG GGC TCA           497
Trp Glu Val Pro Phe Glu Glu Ile Leu Asp Leu Gln Trp Val Gly Ser
            120                 125                 130

GGG GCC CAG GGT GCT GTC TTC CTG GGG CGC TTC CAC GGG GAG GAG GTG           545
Gly Ala Gln Gly Ala Val Phe Leu Gly Arg Phe His Gly Glu Glu Val
        135                 140                 145

GCT GTG AAG AAG GTG CGA GAC CTC AAA GAA ACC GAC ATC AAG CAC TTG           593
Ala Val Lys Lys Val Arg Asp Leu Lys Glu Thr Asp Ile Lys His Leu
150                 155                 160                 165

CGA AAG CTG AAG CAC CCC AAC ATC ATC ACT TTC AAG GGT GTG TGC ACC           641
Arg Lys Leu Lys His Pro Asn Ile Ile Thr Phe Lys Gly Val Cys Thr
                170                 175                 180

CAG GCT CCC TGC TAC TGC ATC CTC ATG GAG TTC TGC GCC CAG GGC CAG           689
Gln Ala Pro Cys Tyr Cys Ile Leu Met Glu Phe Cys Ala Gln Gly Gln
                185                 190                 195

CTG TAT GAG GTA CTG CGG GCT GGC CGC CCT GTC ACC CCC TCC TTA CTG           737
Leu Tyr Glu Val Leu Arg Ala Gly Arg Pro Val Thr Pro Ser Leu Leu
```

```
                      200                           205                                210
GTT  GAC  TGG  TCC  ATG  GGC  ATC  GCT  GGT  GGC  ATG  AAC  TAC  CTG  CAC  CTG      785
Val  Asp  Trp  Ser  Met  Gly  Ile  Ala  Gly  Gly  Met  Asn  Tyr  Leu  His  Leu
     215            220                 225

CAC  AAG  ATT  ATC  CAC  AGG  GAT  CTC  AAG  TCA  CCC  AAC  ATG  CTA  ATC  ACC      833
His  Lys  Ile  Ile  His  Arg  Asp  Leu  Lys  Ser  Pro  Asn  Met  Leu  Ile  Thr
230            235                 240                 245

TAC  GAC  GAT  GTG  GTG  AAG  ATC  TCA  GAT  TTT  GGC  ACT  TCC  AAG  GAG  CTG      881
Tyr  Asp  Asp  Val  Val  Lys  Ile  Ser  Asp  Phe  Gly  Thr  Ser  Lys  Glu  Leu
               250                 255                 260

AGT  GAC  AAG  AGC  ACC  AAG  ATG  TCC  TTT  GCA  GGG  ACA  GTA  GCC  TGG  ATG      929
Ser  Asp  Lys  Ser  Thr  Lys  Met  Ser  Phe  Ala  Gly  Thr  Val  Ala  Trp  Met
               265                 270                 275

GCC  CCT  GAG  GTG  ATC  CGC  AAT  GAA  CCT  GTG  TCT  GAG  AAG  GTC  GAC  ATC      977
Ala  Pro  Glu  Val  Ile  Arg  Asn  Glu  Pro  Val  Ser  Glu  Lys  Val  Asp  Ile
          280                 285                 290

TGG  TCC  TTT  GGC  GTG  GTG  CTA  TGG  GAA  CTG  CTG  ACT  GGT  GAG  ATC  CCC     1025
Trp  Ser  Phe  Gly  Val  Val  Leu  Trp  Glu  Leu  Leu  Thr  Gly  Glu  Ile  Pro
     295                 300                 305

TAC  AAA  GAC  GTA  GAT  TCC  TCA  GCC  ATT  ATC  TGG  GGT  GTG  GGA  AGC  AAC     1073
Tyr  Lys  Asp  Val  Asp  Ser  Ser  Ala  Ile  Ile  Trp  Gly  Val  Gly  Ser  Asn
310                 315                 320                 325

AGT  CTC  CAT  CTG  CCC  GTG  CCC  TCC  AGT  TGC  CCA  GAT  GGT  TTC  AAG  ATC     1121
Ser  Leu  His  Leu  Pro  Val  Pro  Ser  Ser  Cys  Pro  Asp  Gly  Phe  Lys  Ile
               330                 335                 340

CTG  CTT  CGC  CAG  TGC  TGG  AAT  AGC  AAA  CCA  CGA  AAT  CGC  CCA  TCA  TTC     1169
Leu  Leu  Arg  Gln  Cys  Trp  Asn  Ser  Lys  Pro  Arg  Asn  Arg  Pro  Ser  Phe
               345                 350                 355

CGA  CAG  ATC  CTG  CTG  CAT  CTG  GAC  ATT  GCC  TCA  GCT  GAT  GTA  CTC  TCC     1217
Arg  Gln  Ile  Leu  Leu  His  Leu  Asp  Ile  Ala  Ser  Ala  Asp  Val  Leu  Ser
          360                 365                 370

ACA  CCC  CAG  GAG  ACT  TAC  TTT  AAG  TCC  CAG  GCA  GAG  TGG  CGG  GAA  GAA     1265
Thr  Pro  Gln  Glu  Thr  Tyr  Phe  Lys  Ser  Gln  Ala  Glu  Trp  Arg  Glu  Glu
     375                 380                 385

GTA  AAA  CTG  CAC  TTT  GAA  AAG  ATT  AAG  TCA  GAA  GGG  ACC  TGT  CTG  CAC     1313
Val  Lys  Leu  His  Phe  Glu  Lys  Ile  Lys  Ser  Glu  Gly  Thr  Cys  Leu  His
390                 395                 400                 405

CGC  CTA  GAA  GAG  GAA  CTG  GTG  ATG  AGG  AGG  AGG  GAG  GAG  CTC  AGA  CAC     1361
Arg  Leu  Glu  Glu  Glu  Leu  Val  Met  Arg  Arg  Arg  Glu  Glu  Leu  Arg  His
               410                 415                 420

GCC  CTG  GAC  ATC  AGG  GAG  CAC  TAT  GAA  AGG  AAG  CTG  GAG  AGA  GCC  AAC     1409
Ala  Leu  Asp  Ile  Arg  Glu  His  Tyr  Glu  Arg  Lys  Leu  Glu  Arg  Ala  Asn
               425                 430                 435

AAC  CTG  TAT  ATG  GAA  CTT  AAT  GCC  CTC  ATG  TTG  CAG  CTG  GAA  CTC  AAG     1457
Asn  Leu  Tyr  Met  Glu  Leu  Asn  Ala  Leu  Met  Leu  Gln  Leu  Glu  Leu  Lys
          440                 445                 450

GAG  AGG  GAG  CTG  CTC  AGG  CGA  GAG  CAA  GCT  TTA  GAG  CGG  AGG  TGC  CCA     1505
Glu  Arg  Glu  Leu  Leu  Arg  Arg  Glu  Gln  Ala  Leu  Glu  Arg  Arg  Cys  Pro
     455                 460                 465

GGC  CTG  CTG  AAG  CCA  CAC  CCT  TCC  CGG  GGC  CTC  CTG  CAT  GGA  AAC  ACA     1553
Gly  Leu  Leu  Lys  Pro  His  Pro  Ser  Arg  Gly  Leu  Leu  His  Gly  Asn  Thr
470                 475                 480                 485

ATG  GAG  AAG  CTT  ATC  AAG  AAG  AGG  AAT  GTG  CCA  CAG  AAT  CTG  TCA  CCC     1601
Met  Glu  Lys  Leu  Ile  Lys  Lys  Arg  Asn  Val  Pro  Gln  Asn  Leu  Ser  Pro
               490                 495                 500

CAT  AGC  CAA  AGG  CCA  GAT  ATC  CTC  AAG  GCG  GAG  TCT  TTG  CTC  CCT  AAA     1649
His  Ser  Gln  Arg  Pro  Asp  Ile  Leu  Lys  Ala  Glu  Ser  Leu  Leu  Pro  Lys
               505                 510                 515

CTA  GAT  GCA  GCC  CTG  AGT  GGG  GTG  GGG  CTT  CCT  GGG  TGT  CCT  AAG  GCC     1697
Leu  Asp  Ala  Ala  Leu  Ser  Gly  Val  Gly  Leu  Pro  Gly  Cys  Pro  Lys  Ala
```

-continued

```
                520                      525                      530
CCC CCC TCA CCA GGA CGG AGT CGC CGT GGC AAG ACC CGT CAC CGC AAG   1745
Pro Pro Ser Pro Gly Arg Ser Arg Arg Gly Lys Thr Arg His Arg Lys
    535                     540                     545

GCC AGC GCC AAG GGG AGC TGT GGG GAC CTG CCT GGG CTT CGT ACA GCT   1793
Ala Ser Ala Lys Gly Ser Cys Gly Asp Leu Pro Gly Leu Arg Thr Ala
550                     555                     560                 565

GTG CCA CCC CAT GAA CCT GGA GGA CCA GGA AGC CCA GGG GGC CTA GGA   1841
Val Pro Pro His Glu Pro Gly Gly Pro Gly Ser Pro Gly Gly Leu Gly
                570                     575                     580

GGG GGA CCC TCA GCC TGG GAG GCC TGC CCT CCC GCC CTC CGT GGG CTT   1889
Gly Gly Pro Ser Ala Trp Glu Ala Cys Pro Pro Ala Leu Arg Gly Leu
            585                     590                     595

CAT CAT GAC CTC CTG CTC CGC AAA ATG TCT TCA TCG TCC CCA GAC CTG   1937
His His Asp Leu Leu Leu Arg Lys Met Ser Ser Ser Ser Pro Asp Leu
        600                     605                     610

CTG TCA GCA GCA CTA GGG TCC CGG GGC CGG GGG GCC ACA GGC GGA GCT   1985
Leu Ser Ala Ala Leu Gly Ser Arg Gly Arg Gly Ala Thr Gly Gly Ala
    615                     620                     625

GGG GAT CCT GGC TCA CCA CCT CCG GCC CGG GGT GAC ACC CCA CCA AGT   2033
Gly Asp Pro Gly Ser Pro Pro Pro Ala Arg Gly Asp Thr Pro Pro Ser
630                     635                     640                 645

GAG GGC TCA GCC CCT GGC TCC ACC AGC CCA GAT TCA CCT GGG GGA GCC   2081
Glu Gly Ser Ala Pro Gly Ser Thr Ser Pro Asp Ser Pro Gly Gly Ala
                650                     655                     660

AAA GGG GAA CCA CCT CCT CCA GTA GGG CCT GGT GAA GGT GTG GGG CTT   2129
Lys Gly Glu Pro Pro Pro Pro Val Gly Pro Gly Glu Gly Val Gly Leu
            665                     670                     675

CTG GGA ACT GGA AGG GAA GGG ACC TCA GGC CGG GGA GGA AGC CGG GCT   2177
Leu Gly Thr Gly Arg Glu Gly Thr Ser Gly Arg Gly Gly Ser Arg Ala
        680                     685                     690

GGG TCC CAG CAC TTG ACC CCA TCT GCA CTG CTG TAC AGG GCT GCC GTC   2225
Gly Ser Gln His Leu Thr Pro Ser Ala Leu Leu Tyr Arg Ala Ala Val
    695                     700                     705

ACC CGA AGT CAG AAA CGT GGC ATC TCA TCG GAA GAG GAG GAA GGA GAG   2273
Thr Arg Ser Gln Lys Arg Gly Ile Ser Ser Glu Glu Glu Glu Gly Glu
710                     715                     720                 725

GTA GAC AGT GAA GTA GAG CTG ACA TCA AGC CAG AGG TGG CCT CAG AGC   2321
Val Asp Ser Glu Val Glu Leu Thr Ser Ser Gln Arg Trp Pro Gln Ser
                730                     735                     740

CTG AAC ATG CGC CAG TCA CTA TCT ACC TTC AGC TCA GAG AAT CCA TCA   2369
Leu Asn Met Arg Gln Ser Leu Ser Thr Phe Ser Ser Glu Asn Pro Ser
            745                     750                     755

GAT GGG GAG GAA GGC ACA GCT AGT GAA CCT TCC CCC AGT GGC ACA CCT   2417
Asp Gly Glu Glu Gly Thr Ala Ser Glu Pro Ser Pro Ser Gly Thr Pro
        760                     765                     770

GAA GTT GGC AGC ACC AAC ACT GAT GAG CGG CCA GAT GAG CGG TCT GAT   2465
Glu Val Gly Ser Thr Asn Thr Asp Glu Arg Pro Asp Glu Arg Ser Asp
    775                     780                     785

GAC ATG TGC TCC CAG GGC TCA GAA ATC CCA CTG GAC CCA CCT CCT TCA   2513
Asp Met Cys Ser Gln Gly Ser Glu Ile Pro Leu Asp Pro Pro Pro Ser
790                     795                     800                 805

GAG GTC ATC CCT GGC CCT GAA CCC AGC TCC CTG CCC ATT CCA CAC CAG   2561
Glu Val Ile Pro Gly Pro Glu Pro Ser Ser Leu Pro Ile Pro His Gln
                810                     815                     820

GAA CTT CTC AGA GAG CGG GGC CCT CCC AAT TCT GAG GAC TCA GAC TGT   2609
Glu Leu Leu Arg Glu Arg Gly Pro Pro Asn Ser Glu Asp Ser Asp Cys
            825                     830                     835

GAC AGC ACT GAA TTG GAC AAC TCC AAC AGC GTT GAT GCC TTG CGC CCC   2657
Asp Ser Thr Glu Leu Asp Asn Ser Asn Ser Val Asp Ala Leu Arg Pro
```

-continued

```
                840                      845                      850
CCA GCT TCC CTC CCT CCA TGAAAGCCAC TCGTATTCCT TGTACATAGA                      2705
Pro Ala Ser Leu Pro Pro
        855

GAAATATTTA TATGGATTAT ATATATATAC ATATATATAT ATATATGCGC CACATAATCA    2765
ACAGAAAGAT GGGGCTGTCC CAGCCGTAAG TCAGGCTCGA GGGAGACTGA TCCCCTGACC    2825
AATTCACCTG ATAAACTCTA GGGACACTGG CAGCTGTGGA ATGAATGAG GCACAGCCGT    2885
AGAGCTGTGG CTAAGGGCAA GCCCCTTCCT GCCCCACCCC ATTCCTTATA TTCAGCAAGC    2945
AACAAGGCAA TAGAAAAGCC AGGGTTGTCT TTATATTCTT TATCCCCAAA TAATAGGGGG    3005
TGGGGGGAGG GGCGGTGGGA GGGGCAGGAG AGAAAACCAC TTAGACTGCA CTTTTCTGTT    3065
CCGTTTACTC TGTTTACACA TTTTGCACTT GGGAGGAGGG AGGCTAAGGC TGGGTCCTCC    3125
CCTCTGAGGT TTCTCAGGTG GCAATGTAAC TCATTTTTTT GTCCCACCAT TTATCTTCTC    3185
TGCCCAAGCC CTGTCTTAAG GCCCAGGGGG AGGTTAGGAG ACTGATAGCA TGTGATGGCT    3245
CAGGCTGAAG AACCGGGGTT CTGTTTAAGT CCCTGCTTTT ATCCTGGTGC CTGATTGGGG    3305
TGGGGACTGT CCTACTGTAA CCCCTGTGAA AAACCTTGAA AATAACACT CCATGCAGGA    3365
AAAAAAAAAA AAAAAAAAA AAAA                                             3389
```

( 2 ) INFORMATION FOR SEQ ID NO:2:

( i ) SEQUENCE CHARACTERISTICS:
( A ) LENGTH: 859 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ala Cys Leu His Glu Thr Arg Thr Pro Ser Pro Ser Phe Gly
 1               5                  10                  15

Gly Phe Val Ser Thr Leu Ser Glu Ala Ser Met Arg Lys Leu Asp
                20                  25                  30

Pro Asp Thr Ser Asp Cys Thr Pro Glu Lys Asp Leu Thr Pro Thr
                35                  40                  45

His Val Leu Gln Leu His Glu Gln Asp Ala Gly Gly Pro Gly Gly
                50                  55                  60

Ala Ala Gly Ser Pro Glu Ser Arg Ala Ser Arg Val Arg Ala Asp
                65                  70                  75

Glu Val Arg Leu Gln Cys Gln Ser Gly Ser Gly Phe Leu Glu Gly
                80                  85                  90

Leu Phe Gly Cys Leu Arg Pro Val Trp Thr Met Ile Gly Lys Ala
                95                 100                 105

Tyr Ser Thr Glu His Lys Gln Gln Gln Glu Asp Leu Trp Glu Val
               110                 115                 120

Pro Phe Glu Glu Ile Leu Asp Leu Gln Trp Val Gly Ser Gly Ala
               125                 130                 135

Gln Gly Ala Val Phe Leu Gly Arg Phe His Gly Glu Glu Val Ala
               140                 145                 150

Val Lys Lys Val Arg Asp Leu Lys Glu Thr Asp Ile Lys His Leu
               155                 160                 165

Arg Lys Leu Lys His Pro Asn Ile Ile Thr Phe Lys Gly Val Cys
               170                 175                 180

Thr Gln Ala Pro Cys Tyr Cys Ile Leu Met Glu Phe Cys Ala Gln
               185                 190                 195
```

```
Gly Gln Leu Tyr Glu Val Leu Arg Ala Gly Arg Pro Val Thr Pro
                200                 205                 210
Ser Leu Leu Val Asp Trp Ser Met Gly Ile Ala Gly Gly Met Asn
                215                 220                 225
Tyr Leu His Leu His Lys Ile Ile His Arg Asp Leu Lys Ser Pro
                230                 235                 240
Asn Met Leu Ile Thr Tyr Asp Asp Val Val Lys Ile Ser Asp Phe
                245                 250                 255
Gly Thr Ser Lys Glu Leu Ser Asp Lys Ser Thr Lys Met Ser Phe
                260                 265                 270
Ala Gly Thr Val Ala Trp Met Ala Pro Glu Val Ile Arg Asn Glu
                275                 280                 285
Pro Val Ser Glu Lys Val Asp Ile Trp Ser Phe Gly Val Val Leu
                290                 295                 300
Trp Glu Leu Leu Thr Gly Glu Ile Pro Tyr Lys Asp Val Asp Ser
                305                 310                 315
Ser Ala Ile Ile Trp Gly Val Gly Ser Asn Ser Leu His Leu Pro
                320                 325                 330
Val Pro Ser Ser Cys Pro Asp Gly Phe Lys Ile Leu Leu Arg Gln
                335                 340                 345
Cys Trp Asn Ser Lys Pro Arg Asn Arg Pro Ser Phe Arg Gln Ile
                350                 355                 360
Leu Leu His Leu Asp Ile Ala Ser Ala Asp Val Leu Ser Thr Pro
                365                 370                 375
Gln Glu Thr Tyr Phe Lys Ser Gln Ala Glu Trp Arg Glu Glu Val
                380                 385                 390
Lys Leu His Phe Glu Lys Ile Lys Ser Glu Gly Thr Cys Leu His
                395                 400                 405
Arg Leu Glu Glu Glu Leu Val Met Arg Arg Arg Glu Glu Leu Arg
                410                 415                 420
His Ala Leu Asp Ile Arg Glu His Tyr Glu Arg Lys Leu Glu Arg
                425                 430                 435
Ala Asn Asn Leu Tyr Met Glu Leu Asn Ala Leu Met Leu Gln Leu
                440                 445                 450
Glu Leu Lys Glu Arg Glu Leu Leu Arg Arg Glu Gln Ala Leu Glu
                455                 460                 465
Arg Arg Cys Pro Gly Leu Leu Lys Pro His Pro Ser Arg Gly Leu
                470                 475                 480
Leu His Gly Asn Thr Met Glu Lys Leu Ile Lys Lys Arg Asn Val
                485                 490                 495
Pro Gln Asn Leu Ser Pro His Ser Gln Arg Pro Asp Ile Leu Lys
                500                 505                 510
Ala Glu Ser Leu Leu Pro Lys Leu Asp Ala Ala Leu Ser Gly Val
                515                 520                 525
Gly Leu Pro Gly Cys Pro Lys Ala Pro Pro Ser Pro Gly Arg Ser
                530                 535                 540
Arg Arg Gly Lys Thr Arg His Arg Lys Ala Ser Ala Lys Gly Ser
                545                 550                 555
Cys Gly Asp Leu Pro Gly Leu Arg Thr Ala Val Pro Pro His Glu
                560                 565                 570
Pro Gly Gly Pro Gly Ser Pro Gly Gly Leu Gly Gly Gly Pro Ser
                575                 580                 585
Ala Trp Glu Ala Cys Pro Pro Ala Leu Arg Gly Leu His His Asp
```

|     |     |     |     | 590 |     |     |     | 595 |     |     |     | 600 |
|---|---|---|---|---|---|---|---|---|---|---|---|---|
| Leu | Leu | Leu | Arg | Lys | Met | Ser | Ser | Ser | Pro | Asp | Leu | Leu | Ser |
|     |     |     |     | 605 |     |     |     | 610 |     |     |     | 615 |
| Ala | Ala | Leu | Gly | Ser | Arg | Gly | Arg | Gly | Ala | Thr | Gly | Gly | Ala | Gly |
|     |     |     |     | 620 |     |     |     | 625 |     |     |     | 630 |
| Asp | Pro | Gly | Ser | Pro | Pro | Pro | Ala | Arg | Gly | Asp | Thr | Pro | Pro | Ser |
|     |     |     |     | 635 |     |     |     | 640 |     |     |     | 645 |
| Glu | Gly | Ser | Ala | Pro | Gly | Ser | Thr | Ser | Pro | Asp | Ser | Pro | Gly | Gly |
|     |     |     |     | 650 |     |     |     | 655 |     |     |     | 660 |
| Ala | Lys | Gly | Glu | Pro | Pro | Pro | Pro | Val | Gly | Pro | Gly | Glu | Gly | Val |
|     |     |     |     | 665 |     |     |     | 670 |     |     |     | 675 |
| Gly | Leu | Leu | Gly | Thr | Gly | Arg | Glu | Gly | Thr | Ser | Gly | Arg | Gly | Gly |
|     |     |     |     | 680 |     |     |     | 685 |     |     |     | 690 |
| Ser | Arg | Ala | Gly | Ser | Gln | His | Leu | Thr | Pro | Ala | Ala | Leu | Leu | Tyr |
|     |     |     |     | 695 |     |     |     | 700 |     |     |     | 705 |
| Arg | Ala | Ala | Val | Thr | Arg | Ser | Gln | Lys | Arg | Gly | Ile | Ser | Ser | Glu |
|     |     |     |     | 710 |     |     |     | 715 |     |     |     | 720 |
| Glu | Glu | Glu | Gly | Glu | Val | Asp | Ser | Glu | Val | Glu | Leu | Thr | Ser | Ser |
|     |     |     |     | 725 |     |     |     | 730 |     |     |     | 735 |
| Gln | Arg | Trp | Pro | Gln | Ser | Leu | Asn | Met | Arg | Gln | Ser | Leu | Ser | Thr |
|     |     |     |     | 740 |     |     |     | 745 |     |     |     | 750 |
| Phe | Ser | Ser | Glu | Asn | Pro | Ser | Asp | Gly | Glu | Glu | Gly | Thr | Ala | Ser |
|     |     |     |     | 755 |     |     |     | 760 |     |     |     | 765 |
| Glu | Pro | Ser | Pro | Ser | Gly | Thr | Pro | Glu | Val | Gly | Ser | Thr | Asn | Thr |
|     |     |     |     | 770 |     |     |     | 775 |     |     |     | 780 |
| Asp | Glu | Arg | Pro | Asp | Glu | Arg | Ser | Asp | Met | Cys | Ser | Gln | Gly |
|     |     |     |     | 785 |     |     |     | 790 |     |     |     | 795 |
| Ser | Glu | Ile | Pro | Leu | Asp | Pro | Pro | Ser | Glu | Val | Ile | Pro | Gly |
|     |     |     |     | 800 |     |     |     | 805 |     |     |     | 810 |
| Pro | Glu | Pro | Ser | Ser | Leu | Pro | Ile | Pro | His | Gln | Glu | Leu | Leu | Arg |
|     |     |     |     | 815 |     |     |     | 820 |     |     |     | 825 |
| Glu | Arg | Gly | Pro | Pro | Asn | Ser | Glu | Asp | Ser | Asp | Cys | Asp | Ser | Thr |
|     |     |     |     | 830 |     |     |     | 835 |     |     |     | 840 |
| Glu | Leu | Asp | Asn | Ser | Asn | Ser | Val | Asp | Ala | Leu | Arg | Pro | Pro | Ala |
|     |     |     |     | 845 |     |     |     | 850 |     |     |     | 855 |
| Ser | Leu | Pro | Pro |     |     |     |     |     |     |     |     |     |     |     |

( 2 ) INFORMATION FOR SEQ ID NO:3:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear     ( x i ) SEQUENCE DESCRIPTION: SEQ ID NO:3:

CCATGAAAGC CACTCGTATT CCT      23

( 2 ) INFORMATION FOR SEQ ID NO:4:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

TCTTTCTGTT GATTATGTGG CGC 23